(12) United States Patent
Xu et al.

(10) Patent No.: US 12,303,388 B1
(45) Date of Patent: May 20, 2025

(54) VALVE COMPRESSION APPARATUS

(71) Applicant: NANJING DRUM TOWER HOSPITAL, Jiangsu (CN)

(72) Inventors: Can Xu, Jiangsu (CN); Dongjin Wang, Jiangsu (CN)

(73) Assignee: NANJING DRUM TOWER HOSPITAL, Jiangsu (CN)

( * ) Notice: Subject to any disclaimer, the term of this patent is extended or adjusted under 35 U.S.C. 154(b) by 0 days.

(21) Appl. No.: 18/850,457

(22) PCT Filed: Feb. 28, 2024

(86) PCT No.: PCT/CN2024/078949
§ 371 (c)(1),
(2) Date: Sep. 24, 2024

(30) Foreign Application Priority Data

Nov. 14, 2023 (CN) .......................... 202311510115.0

(51) Int. Cl.
*B23P 11/00* (2006.01)
*A61F 2/24* (2006.01)

(52) U.S. Cl.
CPC ................................. *A61F 2/2427* (2013.01)

(58) Field of Classification Search
CPC ....... B23P 11/00; B23P 11/005; B23P 11/027; A61F 2/2427; A61F 2/243
See application file for complete search history.

(56) References Cited

U.S. PATENT DOCUMENTS 4,011,947 A * 3/1977 Sawyer ................. A61F 2/2427
623/2.11

5,725,519 A * 3/1998 Penner .................. A61F 2/9525
606/1

(Continued)

FOREIGN PATENT DOCUMENTS

| CN | 109475414 A | 3/2019 |
|---|---|---|
| CN | 112402056 A | 2/2021 |

(Continued)

*Primary Examiner* — Lee D Wilson
(74) *Attorney, Agent, or Firm* — Muncy, Geissler, Olds & Lowe, P.C.

(57) ABSTRACT

The present invention discloses a valve compression apparatus, belongs to the technical field of medical apparatus and instruments, and includes a compression shell, a communication tube, a funnel tube, a compression arc plate, and a pressing assembly; the communication tube is smoothly connected to a small-diameter end of the funnel tube; two opposite sides of the compression shell are provided with placement ports respectively, one placement port is communicated with the communication tube, and the other placement port is communicated with the funnel tube; a plurality of operation ports are arranged in a circumferential direction of the funnel tube; the pressing assembly includes a traction plate with a slope, an elastic support assembly, and a moving ring; when the moving ring moves in a direction from the communication tube to the funnel tube, the moving ring simultaneously squeezes a plurality of traction plates, to drive the traction plates to move towards the funnel tube; the compression arc plate is in a one-to-one correspondence with the operation port, and is connected to the traction plate through a connecting rod; when the traction plate moves towards the funnel tube, the compression arc plate passes through the operation port and moves towards an axis of the funnel tube, to quickly compress a valve and avoid damage in the valve compression process.

7 Claims, 7 Drawing Sheets

(56) References Cited

U.S. PATENT DOCUMENTS

| | | | |
|---|---|---|---|
| 8,006,535 B2 * | 8/2011 | Righini | A61F 2/2415 |
| | | | 72/402 |
| 10,010,412 B2 * | 7/2018 | Taft | A61F 2/95 |
| 10,716,691 B2 * | 7/2020 | Saar | A61F 2/95 |
| 11,944,559 B2 * | 4/2024 | Dalbow | A61F 2/2418 |
| 2021/0186695 A1 | 6/2021 | Huddleston et al. | |
| 2022/0379091 A1 * | 12/2022 | Hughes | A61F 2/2427 |

FOREIGN PATENT DOCUMENTS

| | | |
|---|---|---|
| CN | 219354280 U | 7/2023 |
| CN | 117323065 A | 1/2024 |
| WO | WO-2022235477 A1 | 11/2022 |

\* cited by examiner

VALVE COMPRESSION APPARATUS

TECHNICAL FIELD

The present invention belongs to the technical field of medical apparatus and instruments, and specifically relates to a valve compression apparatus.

BACKGROUND

In transcatheter valve intervention, pericardium tissue is usually sutured and fixed on a valve frame by using sutures. Before an interventional valve surgery, a special catheter is used to load and transport a valve to a target position for valve release and deployment. In a process of loading and transporting, it is required to minimize damage to the artificial valve.

When the existing artificial valve is loaded, a valve frame loaded with the artificial valve is connected through a connecting structure such as a claw, and the artificial valve is dragged into a compression lumen with a taper inner diameter, so that the artificial valve enters from a large port and exits from a small port of the compression lumen. In a process that the artificial valve is dragged, a tube diameter is continuously reduced to compress a dimension of the artificial valve, so that the artificial valve can be introduced into a catheter and loaded on a transport system. However, the existing valve frame loaded with the artificial valve still has the following problems in the compression process.

The existing valve frame has strong radial supporting force, which causes great resistance in the process that the valve is dragged. In addition, with a continuously reduced tube diameter, the valve frame loaded with the artificial valve compresses the dimension of the artificial valve, and force for pushing the valve frame of the artificial valve to move is uneven. This is easy to cause damage or even fracture to sutures between the artificial valve and the valve frame, and increases costs to use. Therefore, it is necessary to involve a valve compression apparatus in the field of existing medical apparatus and instruments.

SUMMARY

The present invention aims to overcome shortcomings in the prior art and provide a valve compression apparatus, to quickly compress a valve and avoid damage in a valve compression process.

The present invention provides the following technical solutions.

A valve compression apparatus is provided, where the apparatus includes a compression shell, a communication tube, a funnel tube, a compression arc plate, and a pressing assembly; the communication tube is smoothly connected to a small-diameter end of the funnel tube, to form a channel for accommodating a valve: two opposite sides of the compression shell are provided with placement ports respectively, one placement port is communicated with the communication tube, and the other placement port is communicated with a large-diameter end of the funnel tube; and a plurality of operation ports penetrating through a tube wall are arranged in a circumferential direction of the funnel tube:

the pressing assembly includes a traction plate with a slope, an elastic support assembly, and a moving ring: there are a plurality of the traction plates encircling the funnel tube: one end of the elastic support assembly is connected to an inner side of the traction plate, and the other end is installed on a peripheral surface of the communication tube or the funnel tube: the moving ring is sleeved on an outer side of the plurality of traction plates and is able to move along an axial direction of the funnel tube: when the moving ring moves in a direction from the communication tube to the funnel tube, the moving ring simultaneously squeezes the plurality of traction plates, to drive the traction plates to move towards the funnel tube; and the compression arc plate is in a one-to-one correspondence with the operation port, and is connected to the traction plate through a connecting rod; and when the traction plate moves towards the funnel tube, the compression arc plate passes through the operation port and moves towards an axis of the funnel tube.

Preferably, the traction plate includes a first plane portion, a first slope portion, a second plane portion, a second slope portion, and a third plane portion that are successively connected; the first plane portion, the first slope portion, and the second plane portion are located on an outer side of the communication tube: the second slope portion and the third plane portion are located on an outer side of the funnel tube: an inner side of the third plane portion is connected to the connecting rod: an annular inner diameter formed by enclosing of a plurality of the first plane portions is equal to or smaller than an inner diameter of the moving ring: an annular inner diameter formed by enclosing of a plurality of the second plane portions is greater than the inner diameter of the moving ring; and an annular inner diameter formed by enclosing of a plurality of the third plane portions is greater than the annular inner diameter formed by enclosing of the plurality of second plane portions.

Preferably, an end of the first plane portion away from the first slope portion is provided with a first limit plate, and a connecting section between the second plane portion and the second slope portion is provided with a second limit plate; and a dimension of the first limit plate in a radial direction of the communication tube is greater than a radial dimension of the moving ring.

Preferably, there are three groups of the elastic support assembly, a first group of the elastic support assembly is located between the first plane portion and the communication tube, a second group of the elastic support assembly is located between the second plane portion and the communication tube, and a third group of the elastic support assembly is located between the third plane portion and the funnel tube:

the elastic support assembly includes a support spring and a telescopic rod; and the support spring is sleeved on an outer side of the telescopic rod; and the funnel tube is further provided with a plurality of limit blocks: the limit block is in a one-to-one correspondence with the operation port, and the limit block extends from a surface of the funnel tube to the operation port: a side of the third plane portion facing the funnel tube is further provided with a limit rod: the limit rod is connected to a connecting plate; and when the third plane portion moves towards the funnel tube, the connecting plate abuts against a surface of the limit block, to prevent the compression arc plate from moving towards the axis of the funnel tube.

Preferably, an outer side of the compression shell is connected to a handle: a transmission assembly for driving the moving ring to move is arranged in the handle; and the handle is provided with a rotating handwheel, the rotating handwheel is connected to the transmission assembly, and the transmission assembly is driven to drive the moving ring.

Preferably, the transmission assembly includes a first equal-diameter bevel gear, a second equal-diameter bevel gear, a third equal-diameter bevel gear, a fourth equal-diameter bevel gear, and a rotating rod: an operation chamber is arranged in the handle: a handwheel rod is connected on an axis of the rotating handwheel, the handwheel rod is rotatably connected to the handle, and an end away from the rotating handwheel extends into the operation chamber; the end of the handwheel rod extending into the operation chamber is sleeved with the fourth equal-diameter bevel gear: the rotating rod is rotatably connected in the handle, one end of the rotating rod is located in the operation chamber, and the other end is located in the compression shell: the end of the rotating rod located in the operation chamber is provided with a third equal-diameter bevel gear, and the end located in the compression shell is provided with a second equal-diameter bevel gear; and the third equal-diameter bevel gear is meshed with a fourth equal-diameter bevel gear; and the compression shell is further provided with a traction block, one side of the traction block is provided with a slot, a ball screw is rotatably connected in the traction block, a periphery of the moving ring is connected to a connecting arm, and the connecting arm is connected to a moving portion of the ball screw: an end of the ball screw extending out of the traction block is connected to a first equal-diameter bevel gear; and the first equal-diameter bevel gear is meshed with a second equal-diameter bevel gear.

Preferably, an inner wall of the moving ring is provided with a plurality of rotating grooves; and a plurality of compression rollers are rotatably connected in the rotating grooves.

Preferably, a distance between the two placement ports is greater than a sum of axial dimensions of the communication tube and the funnel tube: a conducting assembly is connected in the placement port close to the funnel tube: the conducting assembly includes a conducting tube and a conducting guide rod: the conducting tube is coaxially sleeved in the placement port and is able to translate along an axial direction of the placement port: an inner diameter of the conducting tube is adapted to a big-end inner diameter of the funnel tube: the conducting guide rod penetrates through the compression shell and is able to move back and forth along the compression shell, one end of the conducting guide rod is connected to an end of the conducting tube extending out of the compression shell, and the other end directly faces a limit structure in the compression shell; and when the end of the conducting guide rod located in the compression shell abuts against the limit structure, a nozzle of the conducting tube abuts against a large-diameter nozzle of the funnel tube.

Preferably, the end of the conducting guide rod located in the compression shell is provided with a reset spring and a compression plate: the compression plate is connected to the end of the conducting guide rod extending into the compression shell; and the reset spring is sleeved on an outer side of the conducting guide rod, one end of the reset spring is connected to an inner wall of the compression shell, and the other end is connected to the compression plate.

Preferably, the compression shell is provided with a plurality of limit assemblies encircling outside the conducting tube, and the limit assembly includes a fixing rod and a rotating block; the fixing rod is fixed on an outer surface of the compression shell, and the rotating block is rotatably connected to an end of the fixing rod: an end face of the conducting tube located outside the compression shell is provided with an outwardly extending flange; and when the conducting tube abuts against the funnel tube, the rotating block is able to rotate to an outer side of a flange end face.

The beneficial effects of the present invention compared with the prior art are as follows.

(1) Compression on the valve is performed inside the compression shell, which can avoid an impact of an external environment on an aseptic environment of valve compression: a communication tube and a funnel tube are arranged in the compression shell, and the funnel tube is provided with an operation port: a compression arc plate can penetrate through the operation port to compress the valve: there are a plurality of compression arc plates encircling an outer side of the funnel tube: the outer side of the funnel tube is provided with a traction plate, and the traction plate has a slope: a moving ring is sleeved on an outer side of the traction plate; and when the moving ring moves, the plurality of compression arc plates may be simultaneously squeezed, so that the plurality of compression arc plates can simultaneously squeeze the valve to be compressed. This can quickly compress the valve and avoid damage in the valve compression process.

(2) A conducting assembly is arranged between a placement port of the compression shell and the funnel tube, arrangement of the conducting assembly can ensure enough space inside the compression shell, and it is convenient to place the valve to be compressed in a designated position of the funnel tube: an initial position of a conducting tube is far away from the funnel tube, to avoid interference of the conducting tube on compression of the valve and avoid damage to the valve; and to place the valve to be compressed in the funnel tube conveniently, a limit assembly is further arranged on an outer side of the compression shell, so that automatic reset of the conducting tube can be limited.

Figure 1:
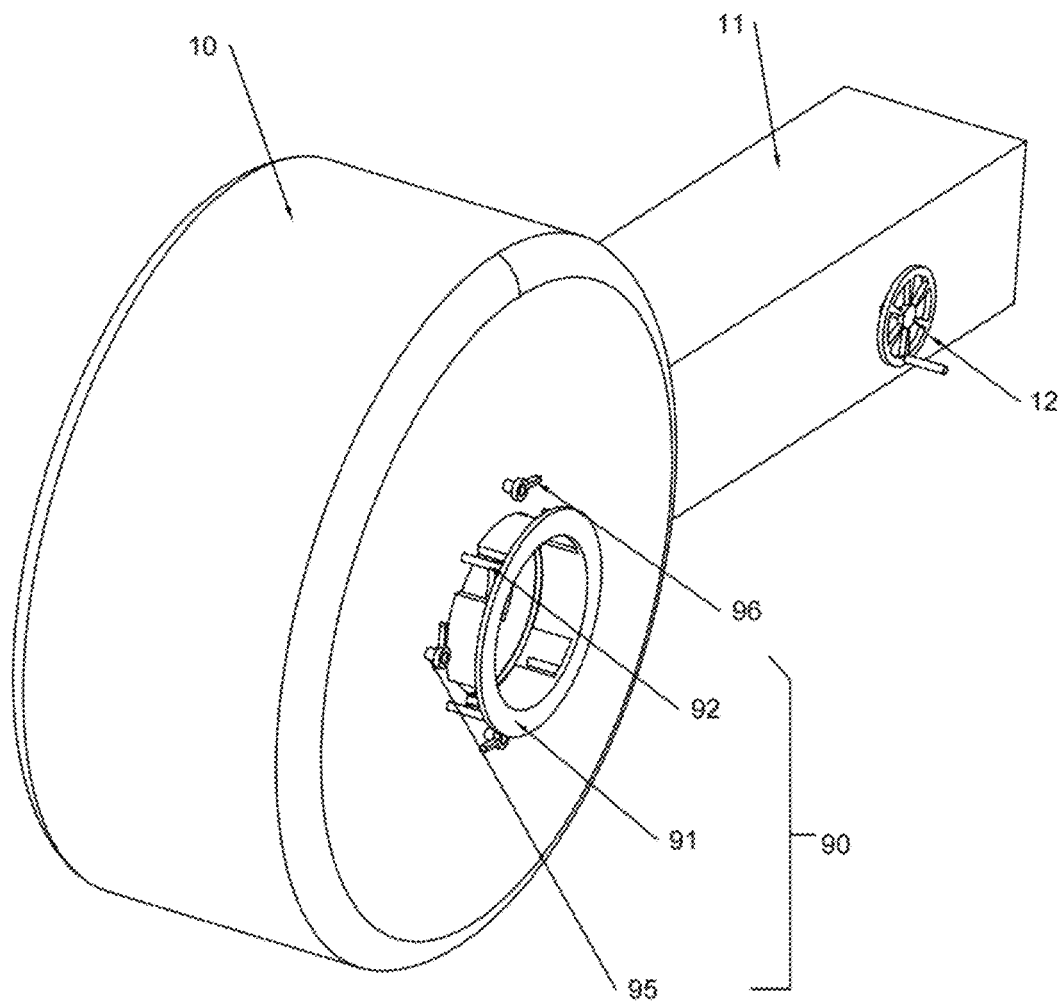
FIG. 1 is a schematic diagram of an overall exterior structure of the present invention.

Reference numerals; 10—compression shell, 101—placement port, 11—handle, 12—rotating handwheel, 13—handwheel rod, 14—operation chamber;

20—communication tube;

30—funnel tube; 31—operation port; 32—limit block;

40—compression arc plate, 41—connecting rod, 42—limit rod, 43—connecting plate;

50—traction plate, 51—first plane portion, 52—first slope portion, 53—second plane portion, 54—second slope portion, 55—third plane portion, 56—first limit plate, 57—second limit plate;
60—elastic support assembly, 61—support spring, 62—telescopic rod;
70—moving ring, 71—connecting arm, 72—compression roller;
80—transmission assembly, 81—first equal-diameter bevel gear, 82—second equal-diameter bevel gear, 83—third equal-diameter bevel gear, 84—fourth equal-diameter bevel gear, 85—rotating rod, 86—traction block, 87—ball screw;
90—conducting assembly, 91—conducting tube, 92—conducting guide rod, 93—reset spring, 94—compression plate, 95—fixing rod, 96—rotating block.

DETAILED DESCRIPTION

The present invention is further explained in detail with reference to the accompanying drawings.

It should be noted that terms such as "up", "down", "left", "right", "front", and "back" in the present invention are only used for convenience of description, and are not used to limit an applicable scope of the present invention. The change or adjustment of a relative relationship should also fall within the applicable scope of the present invention without substantial change in technical content.

As shown in FIG. 1 to FIG. 7, a valve compression apparatus is provided. The apparatus includes a compression shell 10, a communication tube 20, a funnel tube 30, a compression arc plate 40 that are arranged in the compression shell 10, and a pressing assembly.

Figure 3:
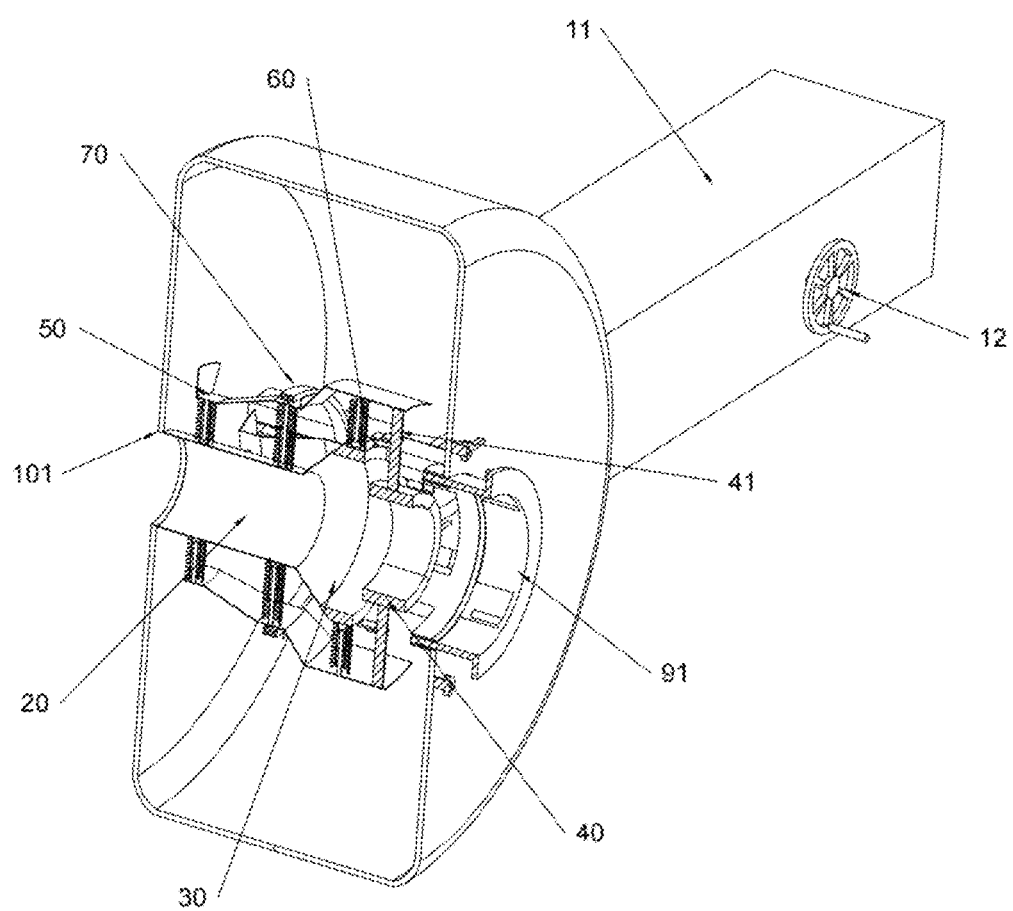
FIG. 3 is a longitudinally sectional view of a compression shell according to the present invention.

As shown in FIG. 3, the communication tube 20 is smoothly connected to a small-diameter end of the funnel tube 30, to form a channel for accommodating a valve: two opposite sides of the compression shell 10 are provided with placement ports 101 respectively, one placement port 101 is communicated with the communication tube 20, and the other placement port 101 is communicated with a large-diameter end of the funnel tube 30: a shape of the compression shell 10 may be one of common shapes such as circle, square, and polygon; and at outer sides of the two placement ports 101, covers or other components detachably connected to the placement ports 101 may be arranged as required, thereby further ensuring an aseptic environment inside the compression shell 10. A plurality of operation ports 31 penetrating through a tube wall are arranged in a circumferential direction of the funnel tube 30; a small diameter of the funnel tube 30 is adapted to an inner diameter of the communication tube 20, the funnel tube 30) and the communication tube 20 are integrally formed or welded together, and a connection gap between the funnel tube 30 and the communication tube 20 is smooth, that is, the gap between the communication tube 20 and the funnel tube 30 may not cause damage to the valve: a big-end inner diameter of the funnel tube 30 can accommodate an uncompressed valve, and the inner diameter of the communication tube 20 can accommodate a compressed valve; and the placement port 101 near the funnel tube 30 is used to send in the uncompressed valve, the placement port 101 near the communication tube 20 is used to send out the compressed valve, and the compressed valve is taken out from the placement port 101. Reference may be made to the prior art.

Figure 4:
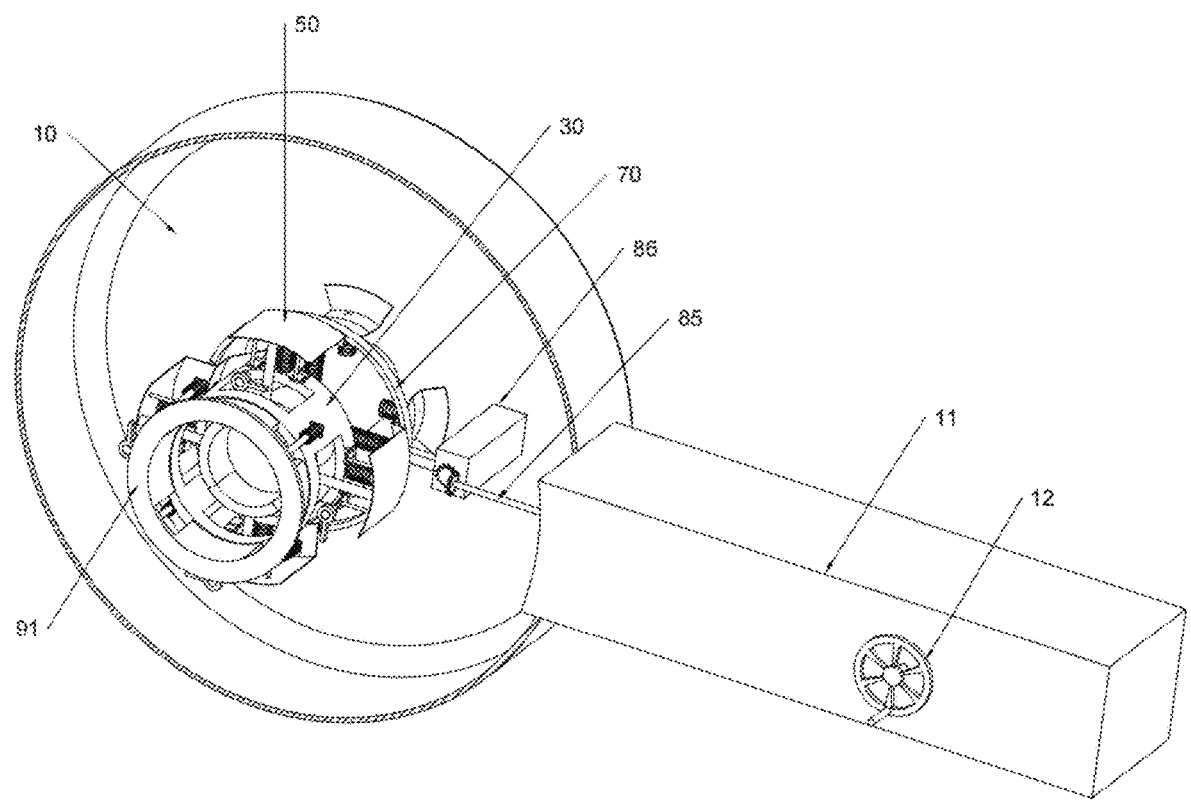
FIG. 4 is a schematic diagram of a structure of a compression shell in a sectional part according to the present invention.
Figure 5:
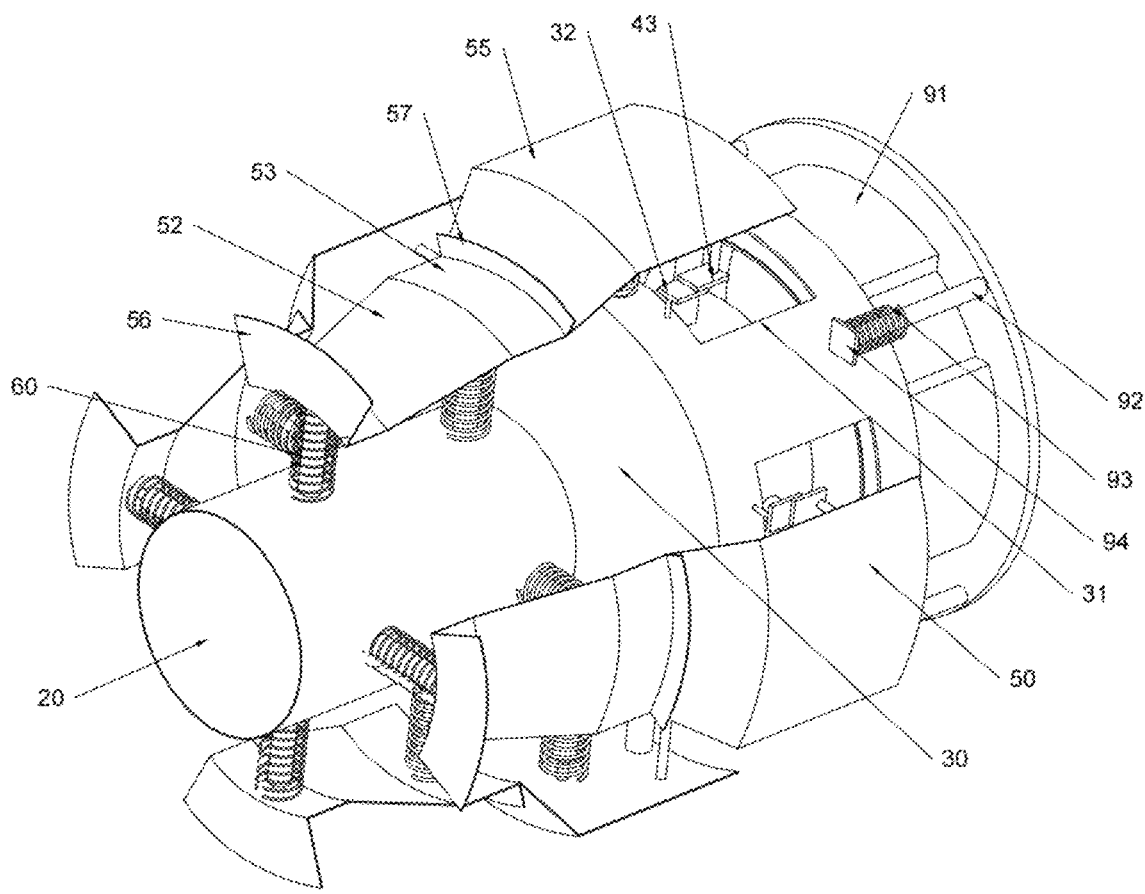
FIG. 5 is a schematic diagram of an interior of a compression shell according to the present invention.

As shown in FIG. 4 and FIG. 5, the pressing assembly includes a traction plate 50 with a slope, an elastic support assembly 60, and a moving ring 70: there are a plurality of the traction plates 50 encircling the funnel tube 30, one end of the elastic support assembly 60 is connected to an inner side of the traction plate 50, and the other end is installed on a peripheral surface of the communication tube 20 or the funnel tube 30; the moving ring 70 is sleeved on an outer side of the plurality of traction plates 50 and is able to move along an axial direction of the funnel tube 30; when the moving ring 70 moves in a direction from the communication tube 20 to the funnel tube 30, the moving ring 70 simultaneously squeezes the plurality of traction plates 50, to drive the traction plates 50 to move towards the funnel tube 30; and the elastic support assembly 60 can support the traction plate 50 and can drive the traction plate 50 to return when pressing force of the moving ring 70 on the traction plate 50 disappears.

The compression arc plate 40 is in a one-to-one correspondence with the operation port 31, and is connected to the traction plate 50 through a connecting rod 41: a quantity of the compression arc plates 40 is in a one-to-one correspondence with a quantity of the operation ports 31, there may be three, four, or six compression arc plates 40, and the quantity of compression arc plates 40 is in a one-to-one correspondence with a quantity of the connecting rods 41: when the traction plate 50 moves towards the funnel tube 30, that is, when the traction plate 50 squeezes the elastic support assembly 60, the compression arc plate 40 passes through the operation port 31 and moves towards an axis of the funnel tube 30, when the plurality of compression arc plates 40 simultaneously move towards the axis of the funnel tube 30, the valve placed at the large-diameter end of the funnel tube 30 can be compressed, the compression arc plate 40 is used for squeezing, so that the valve can be prevented from being damaged, and the plurality of compression arc plates 40 act at the same time, to ensure stability of the valve during compression; and the elastic support assembly 60 can also buffer movement of the compression arc plates 40 during the valve compression process, to further avoid valve damage.

Figure 6:
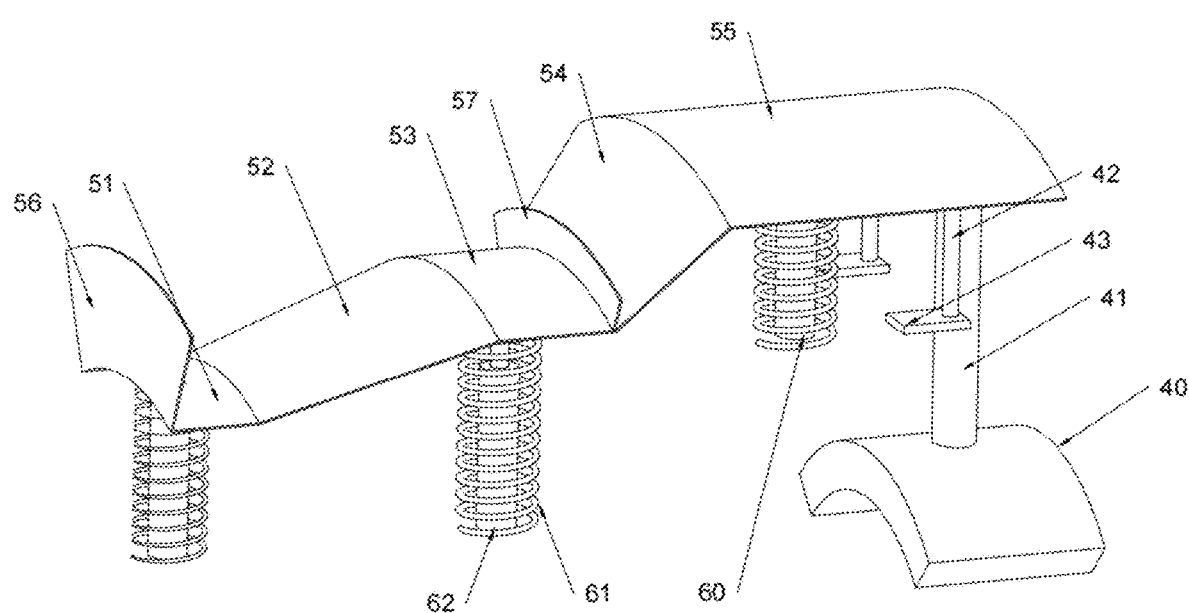
FIG. 6 is a schematic diagram of an overall structure of a traction plate according to the present invention.

Specifically, as shown in FIG. 5 and FIG. 6, the traction plate 50 includes a first plane portion 51, a first slope portion 52, a second plane portion 53, a second slope portion 54, and a third plane portion 55 that are successively connected: the first plane portion 51, the first slope portion 52, the second plane portion 53, the second slope portion 54, and the third plane portion 55 are all arc-shaped in cross section in a radial direction of the communication tube 20, and are connected by welding or integrally formed: the first plane portion 51, the first slope portion 52, and the second plane portion 53 are located on an outer side of the communication tube 20; the second slope portion 54 and the third plane portion 55 are located on an outer side of the funnel tube 30; an inner side of the third plane portion 55 is connected to the connecting rod 41, and an annular inner diameter formed by enclosing of a plurality of the first plane portions 51 is equal to or smaller than an inner diameter of the moving ring 70; an annular inner diameter (before compression) formed by enclosing of a plurality of the second plane portions 53 is greater than the inner diameter of the moving ring 70; and an annular inner diameter formed by enclosing of a plurality of the third plane portions 55 is greater than the annular inner diameter formed by enclosing of the plurality of second plane portions 53, that is, in a process that the moving ring 70 moves from the first plane portion 51 to the second plane portion 53, the traction plate 50 is squeezed as a whole, so that the traction plate 50 drives the compression arc plates 40 to press the valve.

In some other embodiments, an end of the first plane portion 51 away from the first slope portion 52 is provided with a first limit plate 56, and a connecting section between the second plane portion 53 and the second slope portion 54 is provided with a second limit plate 57: a dimension of the first limit plate 56 in a radial direction of the communication tube 20 is greater than a dimension of the second limit plate 57 in the radial direction of the communication tube 20; and both dimensions of the first limit plate 56 and the second limit plate 57 in the radial direction of the communication tube 20 are greater than a radial dimension of the moving ring 70, the first limit plate 56 and the second limit plate 57 can prevent the moving ring 70 from separating from the traction plate 50, and the second limit plate 57 can have a specific limit on a moving distance of the moving ring 70. Certainly, in other embodiments, the dimension of the first limit plate 56 in the radial direction of the communication tube 20 is greater than the radial dimension of the moving ring 70, the dimension of the second limit plate 57 in the radial direction of the communication tube 20 is smaller than the radial dimension of the moving ring 70, and the dimension of the second limit plate 57 in the radial direction of the communication tube 20) is smaller than a distance from the second plane portion 53 to the third plane portion 55 in the radial direction of the communication tube 20, that is, the moving ring 70 may penetrate through the second limit plate 57 and move to the third plane portion 55, to drive the third plane portion 55 to further drive the compression arc plate 40 to squeeze the valve, or to compress valves with different dimensions according to different compression requirements.

In this embodiment, there are three groups of the elastic support assembly 60, a first group of the elastic support assembly 60 is located between the first plane portion 51 and the communication tube 20, a second group of the elastic support assembly 60 is located between the second plane portion 53 and the communication tube 20, and a third group of the elastic support assembly 60 is located between the third plane portion 55 and the funnel tube 30; a quantity of elastic support assemblies 60 is the same as that of traction plates 50; each group of the elastic support assembly 60 includes a support spring 61 and a telescopic rod 62: the support spring 61 is sleeved on an outer side of the telescopic rod 62: one end of the telescopic rod 62 and one end of the support spring 61 are installed on an inner surface of the traction plate 50, and the other end is separately installed on a surface of the communication tube 20 or the funnel tube 30; and a moving distance of the traction plate 50, that is, a moving distance of the compression arc plate 40, may be controlled by using a maximum telescopic height of the telescopic rod 62, and certainly, the moving distance of the compression arc plate 40 may also be controlled in other limit manners.

Further, the funnel tube 30 is further provided with a plurality of limit blocks 32; the limit block 32 is in a one-to-one correspondence with the operation port 31, and the limit block 32 extends from a surface of the funnel tube 30 to the operation port 31: a side of the third plane portion 55 facing the funnel tube 30 is further provided with a limit rod 42; the limit rod 42 is connected to a connecting plate 43; and when the third plane portion 55 moves towards the funnel tube 30, the connecting plate 43 abuts against a surface of the limit block 32, to prevent the compression arc plate 40 from moving towards the axis of the funnel tube 30.

Figure 2:
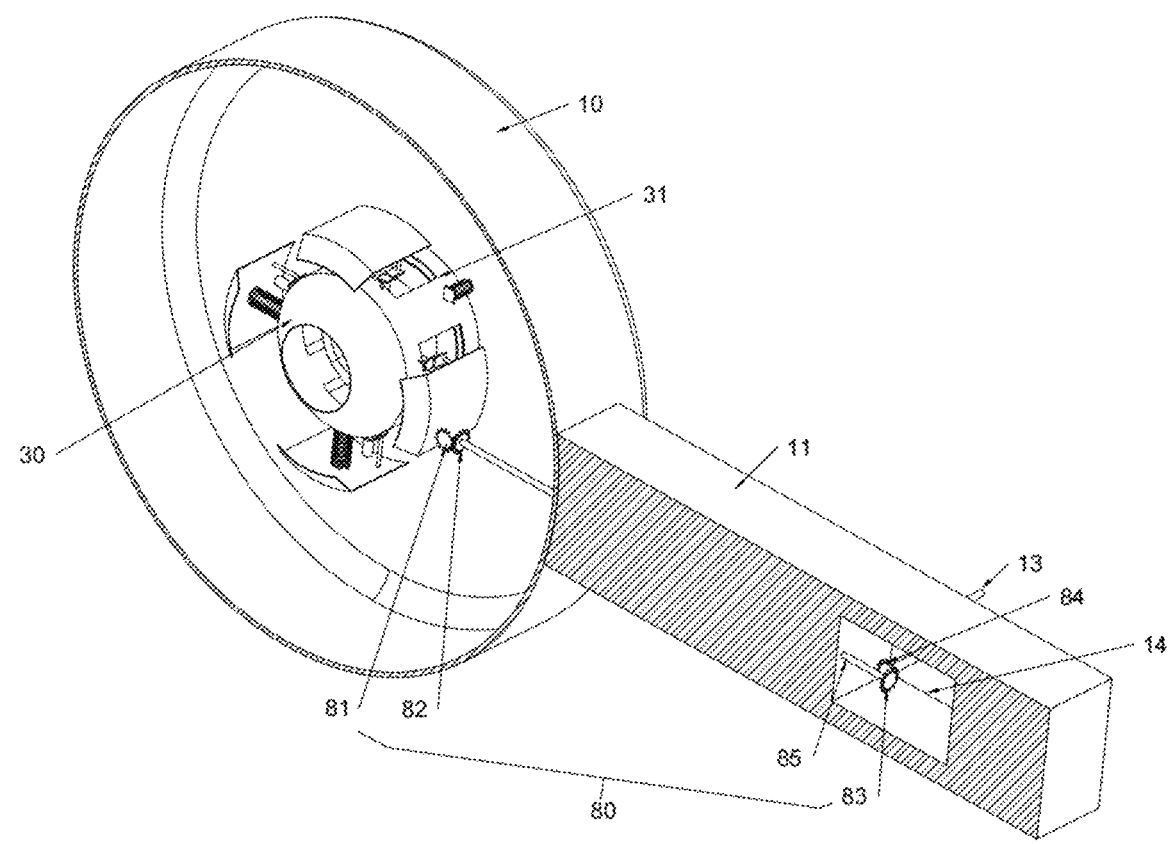
FIG. 2 is a schematic diagram of a sectional structure from a direction of a connecting surface between a communication tube and a funnel tube according to the present invention.
Figure 7:
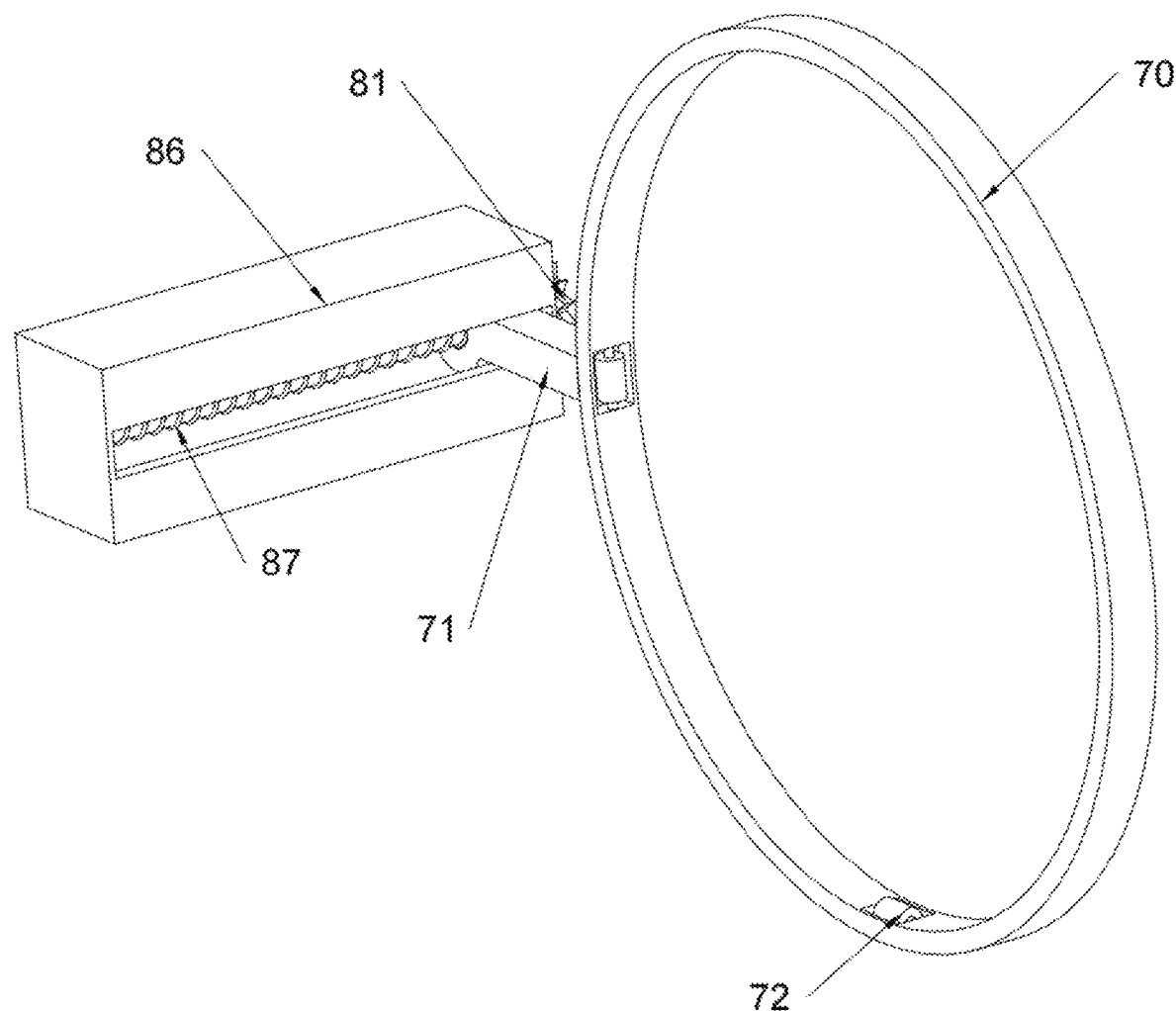
FIG. 7 is a schematic diagram of a partial structure of a transmission assembly according to the present invention.

In some other embodiments, refer to FIG. 2 and FIG. 7, an outer side of the compression shell 10 is connected to a handle 11: a transmission assembly 80 for driving the moving ring 70 to move is arranged in the handle 11; and the handle 11 is provided with a rotating handwheel 12, the rotating handwheel 12 is connected to the transmission assembly 80, and the transmission assembly 80 is driven by manual rotation of the rotating handwheel 12, to drive the moving ring 70 to move.

Specifically, the transmission assembly 80 includes a first equal-diameter bevel gear 81, a second equal-diameter bevel gear 82, a third equal-diameter bevel gear 83, a fourth equal-diameter bevel gear 84, and a rotating rod 85: an operation chamber 14 is arranged in the handle 11: a handwheel rod 13 is connected on an axis of the rotating handwheel 12, the handwheel rod 13 is rotatably connected to the handle 11, and an end away from the rotating handwheel 12 extends into the operation chamber 14: the end of the handwheel rod 13 extending into the operation chamber 14 is sleeved with the fourth equal-diameter bevel gear 84: through the rotating handwheel 12, the handwheel rod 13 drives the fourth equal-diameter bevel gear 84 to rotate synchronously, and there is no relative movement between the rotating handwheel 12 and the handwheel rod 13: the rotating rod 85 is rotatably connected in the handle 11, one end of the rotating rod 85 is located in the operation chamber 14, and the other end is located in the compression shell 10; the end of the rotating rod 85 located in the operation chamber 14 is provided with a third equal-diameter bevel gear 83, and the end located in the compression shell 10 is provided with a second equal-diameter bevel gear 82; and the third equal-diameter bevel gear 83 is meshed with a fourth equal-diameter bevel gear 84; and axes of the rotating rod 85 and the handwheel rod 13 are perpendicular to each other, the compression shell 10 is further provided with a traction block 86, one side of the traction block 86 is provided with a slot, a ball screw 87 is rotatably connected in the traction block 86, an axial direction of the ball screw 87 is parallel to an axial direction of the handwheel rod 13, a periphery of the moving ring 70 is connected to a connecting arm 71, and the connecting arm 71 is connected to a moving portion of the ball screw 87, that is, an end of the connecting arm 71 extends into the traction block 86 and is screwed with the ball screw 87; an end of the ball screw 87 extending out of the traction block 86 is connected to a first equal-diameter bevel gear 81: the first equal-diameter bevel gear 81 is meshed with a second equal-diameter bevel gear 82; and meshing is completed by two pairs of equal-diameter bevel gears meshing with each other, to ensure accuracy of the moving distance of the moving ring 70 and facilitate controlling start and stop of the moving ring 70.

In some other embodiments, an inner wall of the moving ring 70 is provided with a plurality of rotating grooves; and a plurality of compression rollers 72 are rotatably connected in the rotating grooves, and arrangement of the compression rollers 72 can change moving friction between the moving ring 70 and the traction plate 50 into rolling friction and reduce the friction.

In some other embodiments, a distance between the two placement ports 101 is greater than a sum of axial dimensions of the communication tube 20 and the funnel tube 30, and in this way, there can be enough space inside the compression shell 10: a conducting assembly 90 is connected in the placement port 101 close to the funnel tube 30; the conducting assembly 90 is provided to facilitate placement of a valve to be compressed at a designated position of the funnel tube 30; the conducting assembly 90 includes a conducting tube 91 and a conducting guide rod 92: the conducting tube 91 is coaxially sleeved in the placement port 101 and is able to translate along an axial direction of the placement port 101: an inner diameter of the conducting tube 91 is adapted to a big-end inner diameter of the funnel tube 30; the conducting guide rod 92 penetrates through the compression shell 10 and is able to move back and forth along an axial direction of the compression shell 10 (namely, the axial direction of the placement port 101), refer to the prior art for a movable connection manner of the conducting guide rod 92 and the conducting tube 91 separately with the compression shell 10, one end of the conducting guide rod 92 is connected to an end of the conducting tube 91 extending out of the compression shell 10, and the other end directly faces a limit structure in the compression shell 10; and when the end of the conducting guide rod 92 located in the compression shell 10 abuts against the limit structure, a nozzle of the conducting tube 91 abuts against a large-diameter nozzle of the funnel tube 30. The limit structure may be a fixed structure directly fixed in the compression shell, or a connecting rod between the compression arc plate and the traction plate, as long as the guide rod may be limited.

Specifically, the end of the conducting guide rod 92 located in the compression shell 10 is provided with a reset spring 93 and a compression plate 94: the compression plate 94 is connected to the end of the conducting guide rod 92 extending into the compression shell 10; and the reset spring 93 is sleeved on an outer side of the conducting guide rod 92, one end of the reset spring is connected to an inner wall of the compression shell 10, the other end is connected to the compression plate 94, and the compression plate 94 can increase a contact area between the conducting guide rod 92 and the connecting rod 41.

Specifically, the compression shell 10 is provided with a plurality of limit assemblies encircling outside the conducting tube 91, and the limit assembly includes a fixing rod 95 and a rotating block 96: the fixing rod 95 is fixed on an outer surface of the compression shell 10, and the rotating block 96 is rotatably connected to an end of the fixing rod 95: an end face of the conducting tube 91 located outside the compression shell 10 is provided with an outwardly extending flange; and when the conducting tube 91 abuts against the funnel tube 30, the rotating block 96 is able to rotate to an outer side of a flange end face, to avoid resetting of the conducting tube 91.

An operating process of the present invention is as follows: a valve to be compressed is placed at the large-diameter end of the funnel tube 30, the rotating handwheel 12 is manually rotated, the rotating handwheel 12 drives the ball screw 87 to rotate, and under the action of the ball screw 87, the moving ring 70 is driven to move from the first plane portion 51 to the second plane portion 53. During moving, the moving ring 70 simultaneously squeezes a plurality of first slope portions 52 encircling outside the communication tube 20. The first slope portion 52 drives the third plane portion 55 to move towards the axis of the funnel tube 30, and the action of the third plane portion 55 drives the compression arc plate 40 to pass through the operation port 31, to compress the valve located in the funnel tube 30. When the connecting plate 43 abuts against the surface of the limit block 32, compression on the valve is completed, and the compressed valve may be taken out according to the prior art. When the compression is completed, and all components need to be reset, a reverse operation may be performed.

When the valve to be compressed is placed in the funnel tube 30 through the conducting assembly 90, the conducting tube 91 is pressed, so that the conducting tube 91 approaches the funnel tube 30 along the axial direction of the placement port 101, and the conducting guide rod 92 also moves into the compression shell 10 synchronously. When the compression plate 94 at the tail of the conducting guide rod 92 abuts against the connecting rod 41, the rotating block 96 is rotated, so that the rotating block 96 limits the action of the conducting tube 91: the valve to be compressed is placed in the conducting tube 91 communicating with the funnel tube 30, and the valve to be compressed is pushed to the funnel tube 30; and when the valve to be compressed reaches a target position for compressing, the rotating block 96 is reversely rotated to release restriction of the rotating block 96 on the conducting tube 91. Under the action of the reset spring 93, the conducting tube 91 drives the conducting guide rod 92 to reset, and the conducting tube 91 is far away from the funnel tube 30, to avoid an impact on the compression process.

Each embodiment of this specification is described in a progressive manner, each embodiment focuses on the difference from other embodiments, and the same and similar parts between the embodiments may refer to each other.

What is described above are only preferred embodiments of the present invention, and the protection scope of the present invention is not limited to the foregoing embodiments. All technical solutions under the idea of the present invention fall within the protection scope of the present invention. It should be noted that several improvements and refinements made by a person of ordinary skill in the art without departing from the principles described in the present invention shall fall within the protection scope of the present invention.

What is claimed is:

1. A valve compression apparatus, wherein the apparatus comprises a compression shell, a communication tube, a funnel tube, a compression arc plate, and a pressing assembly; the communication tube is smoothly connected to a small-diameter end of the funnel tube, to form a channel for accommodating a valve; two opposite sides of the compression shell are provided with placement ports respectively, one placement port is communicated with the communication tube, and the other placement port is communicated with a large-diameter end of the funnel tube; and a plurality of operation ports penetrating through a tube wall are arranged in a circumferential direction of the funnel tube;

the pressing assembly comprises a traction plate with a slope, an elastic support assembly, and a moving ring; there are a plurality of the traction plates encircling the funnel tube; one end of the elastic support assembly is connected to an inner side of the traction plate, and the other end is installed on a peripheral surface of the communication tube or the funnel tube; the moving ring is sleeved on an outer side of the plurality of traction plates and is able to move along an axial direction of the funnel tube; when the moving ring moves in a direction from the communication tube to the funnel tube, the moving ring simultaneously squeezes the plurality of traction plates, to drive the traction plates to move towards the funnel tube; and the compression arc plate is in a one-to-one correspondence with the operation port, and is connected to the traction plate through a connecting rod; and when the traction plate moves towards the funnel tube, the compression arc plate passes through the operation port and moves towards an axis of the funnel tube.

2. The valve compression apparatus according to claim 1, wherein the traction plate comprises a first plane portion, a first slope portion, a second plane portion, a second slope portion, and a third plane portion that are successively connected; the first plane portion, the first slope portion, and the second plane portion are located on an outer side of the communication tube; the second slope portion and the third plane portion are located on an outer side of the funnel tube; an inner side of the third plane portion is connected to the connecting rod; an annular inner diameter formed by enclosing of a plurality of the first plane portions is equal to or smaller than an inner diameter of the moving ring; an annular inner diameter formed by enclosing of a plurality of the second plane portions is greater than the inner diameter of the moving ring; and an annular inner diameter formed by enclosing of a plurality of the third plane portions is greater than the annular inner diameter formed by enclosing of the plurality of second plane portions.

3. The valve compression apparatus according to claim 2, wherein an end of the first plane portion away from the first slope portion is provided with a first limit plate, and a connecting section between the second plane portion and the second slope portion is provided with a second limit plate; and a dimension of the first limit plate in a radial direction of the communication tube is greater than a radial dimension of the moving ring.

4. The valve compression apparatus according to claim 2, wherein there are three groups of the elastic support assembly, a first group of the elastic support assembly is located between the first plane portion and the communication tube, a second group of the elastic support assembly is located between the second plane portion and the communication tube, and a third group of the elastic support assembly is located between the third plane portion and the funnel tube;

the elastic support assembly comprises a support spring and a telescopic rod; and the support spring is sleeved on an outer side of the telescopic rod; and the funnel tube is further provided with a plurality of limit blocks; the limit block is in a one-to-one correspondence with the operation port, and the limit block extends from a surface of the funnel tube to the operation port; a side of the third plane portion facing the funnel tube is further provided with a limit rod; the limit rod is connected to a connecting plate; and when the third plane portion moves towards the funnel tube, the connecting plate abuts against a surface of the limit block, to prevent the compression arc plate from moving towards the axis of the funnel tube.

5. The valve compression apparatus according to claim 1, wherein an outer side of the compression shell is connected to a handle; a transmission assembly for driving the moving ring to move is arranged in the handle; and the handle is provided with a rotating handwheel, and the rotating handwheel is connected to the transmission assembly.

6. The valve compression apparatus according to claim 5, wherein the transmission assembly comprises a first equal-diameter bevel gear, a second equal-diameter bevel gear, a third equal-diameter bevel gear, a fourth equal-diameter bevel gear, and a rotating rod; an operation chamber is arranged in the handle; a handwheel rod is connected on an axis of the rotating handwheel, the handwheel rod is rotatably connected to the handle, and an end away from the rotating handwheel extends into the operation chamber; the end of the handwheel rod extending into the operation chamber is sleeved with the fourth equal-diameter bevel gear; the rotating rod is rotatably connected in the handle, one end of the rotating rod is located in the operation chamber, and the other end is located in the compression shell; the end of the rotating rod located in the operation chamber is provided with a third equal-diameter bevel gear, and the end located in the compression shell is provided with a second equal-diameter bevel gear; and the third equal-diameter bevel gear is meshed with a fourth equal-diameter bevel gear; and the compression shell is further provided with a traction block, one side of the traction block is provided with a slot, a ball screw is rotatably connected in the traction block, a periphery of the moving ring is connected to a connecting arm, and the connecting arm is connected to a moving portion of the ball screw; an end of the ball screw extending out of the traction block is connected to a first equal-diameter bevel gear; and the first equal-diameter bevel gear is meshed with a second equal-diameter bevel gear.

7. The valve compression apparatus according to claim 1, wherein an inner wall of the moving ring is provided with a plurality of rotating grooves; and a plurality of compression rollers are rotatably connected in the rotating grooves.

\* \* \* \* \*